US010709802B1

(12) United States Patent
Epperley

(10) Patent No.: US 10,709,802 B1
(45) Date of Patent: Jul. 14, 2020

(54) WATER AND ENERGY EFFICIENT MEAT PROCESSING TOOL SANITIZER

(71) Applicant: Randall L. Epperley, Hooker, OK (US)

(72) Inventor: Randall L. Epperley, Hooker, OK (US)

( * ) Notice: Subject to any disclaimer, the term of this patent is extended or adjusted under 35 U.S.C. 154(b) by 0 days.

(21) Appl. No.: 16/560,289

(22) Filed: Sep. 4, 2019

(51) Int. Cl.
*A61L 2/04* (2006.01)
*A61L 2/24* (2006.01)
*A61L 2/28* (2006.01)
*A47L 15/00* (2006.01)

(52) U.S. Cl.
CPC ................................. *A61L 2/04* (2013.01);
*A61L 2/24* (2013.01); *A61L 2202/121* (2013.01); *A61L 2202/122* (2013.01); *A61L 2202/14* (2013.01); *A61L 2202/17* (2013.01)

(58) Field of Classification Search
CPC ........................................................ A61L 2/04
USPC ............................................................ 422/292
See application file for complete search history.

(56) References Cited

U.S. PATENT DOCUMENTS

| | | | | |
|---|---|---|---|---|
| 4,237,912 A * | 12/1980 | Hill | ............................ | A61L 2/04 134/112 |
| 6,325,080 B1 * | 12/2001 | Held | ........................ | A61B 1/123 134/166 R |
| 10,104,867 B2 | 10/2018 | Gabriel et al. | | |
| 10,244,751 B2 | 4/2019 | Herdt et al. | | |
| 2002/0001537 A1 * | 1/2002 | Hlebovy | ............ | A61B 1/00057 422/28 |
| 2005/0000916 A1 | 1/2005 | Ottersbach et al. | | |
| 2010/0252074 A1 * | 10/2010 | Sewake | .................. | A61B 1/123 134/19 |

OTHER PUBLICATIONS

Whitten et al., Chemistry, 10th edition, 2014, Brooks/Cole, p. 31 (Year: 2014).*
HTP; "Phoenix 316L Stainless Steel Gas Fired Water Heater".
Foundation for Meat & Poultry Research Education; "Sanitary Equipment Design Principles: Checklist & Glossary", Jan. 2014.
Cogemat; "Pig slaughter lines", retrieved on Aug. 14, 2019 from http://www.slaughterhouseequipments.com.

(Continued)

*Primary Examiner* — Kevin Joyner
*Assistant Examiner* — Holly Kipourous
(74) *Attorney, Agent, or Firm* — Robert H. Frantz

(57) ABSTRACT

A hot-water immersion sanitizing system has a primary basin for receiving an unsanitary tool or machine component; a thermostatically-controlled valve with a first temperature setpoint, configured to conduct water from a hot water water source to the primary basin until a thermocouple senses a temperature within the primary basin has reached at least the first temperature setpoint, to interrupt flow to the primary basin upon the thermocouple sensing at least the first temperature setpoint; and an overflow drain to exhaust water while the thermostatically-controlled valve is open; thereby automatically maintaining temperature of water held in the primary basin for immersion sanitizing tools and parts at a water temperature of the first temperature setpoint or greater while automatically selectively interrupting flow of water from the water source under thermostatic control.

7 Claims, 3 Drawing Sheets

(56) References Cited

OTHER PUBLICATIONS

Smoky Lake Maple; "Water jacketed draw-off tank", retrieved Aug. 14, 2019 from https://www.smokylakemaple.com.
Hydro Systems; "Sinkmaster: Accurately fills large sinks".
Schmidt, Ronald H.; Basic elements of equipment cleaning and sanitizing in food processing and handling operations; retrieved on Aug. 9, 2019 from https://edis.ifas.ufi.edu/pdffiles/FS/FS07700.pdf.
Omcan Inc.; "Knife Sanitizer".
Mikel, William Benjy; "Meat Plan Sanitation"; retrieved on Aug. 9, 2019 from http://porkgateway.org/resource/meat-plant-sanitation/.
Parker Hannifin; "General Purpose Solenoid Valves: two-way solenoid valves—Type I, normally closed only"; p. 33.
supplyhouse.com; "G23-24V Solenoice Coil for General Purpose Valve", SKU: 77300, Parker Hannifin.
Honeywell; "L4006, 7, 8 Aquastat [TM] Controllers: Product Data", copyright 2006.

* cited by examiner

WATER AND ENERGY EFFICIENT MEAT PROCESSING TOOL SANITIZER

FIELD OF THE INVENTION

The invention generally relates technologies to reduce and minimize water and energy consumption for sanitization of handling and processing tools, such as knives and cutters, for meat processing and preparation facilities.

BACKGROUND OF INVENTION

Persons and companies engaged in meat processing, butchering, preparation and handling must take great care to maintain sanitary facilities and equipment. Even minor contaminations can lead to serious public health consequences because of the number of animals and pounds of meat which are produced from a single facility in a single day, whether it is a small, medium or large scale enterprise. The Centers for Disease Control estimated in 2001 that several million Americans are sickened by food borne illness annually, according to a report entitled "Factsheet: Meat Plant Sanitation" by William Benjy Mikel of the University of Kentucky. Product recalls are very expensive, and loss of reputation to brand names can lead to revenue loss and job loss.

For the purposes of this disclosure, the term "sanitize" and its related terms will be used to refer to the process of exposing handling and processing tools, such as knives, shears, clippers, clamps, etc., to water heated to 180° F., per various governmental agencies and industry standards organizations. Sanitization is not to be construed as sterilization, the latter of which generally involves use of chemicals other than water, much greater levels of heat, and tool exposure of much greater periods of time than sanitization. Sanitization is suitable for cleaning a tool, such as a knife, during the work shift, which may be performed if the tool comes in contact with certain unsanitary parts, organs, or glands of an animal being processed. Sterilization is generally performed between shifts, such as overnight.

According to a paper entitled "Basic Elements of Equipment Cleaning and Sanitizing in Food Processing and Handling Operations" by Ronald H. Schmidt, professor at the Food Science and Human Nutrition Department of the University of Florida, Gainesville, cleaning frequency must be clearly defined for each processing stage, step or workstation, and should include the steps of rinsing, cleaning, rinsing, and sanitizing, in that order. The objectives of this level of cleaning are to remove food nutrients that bacteria could use to grow, and to kill any bacteria which are present on a surface or tool. Schmidt differentiates the terms sterilize, disinfect and sanitize as follows: sterilization is a statistical status of destroying and removing all living organisms, disinfection refers to inanimate objects (tools, machines, etc.) and destruction of all vegetative cells, and sanitization refers to reduction of microorganisms to a level considered safe for an intended purpose according to public policy. Schmidt notes that commonly-used hot-water sanitizing using immersion of small parts such as knives can achieve sanitary status of the parts and tools through use of 180° F. water. Lower temperatures of water can be used, if coupled with longer immersion or exposure times, reaching into the range of 15-20 minutes for some types of components.

As such, heating of water to target temperatures, and consumption of that water for sterilization in medium- and large-scale meat processing, handling, preparation and butchering facilities can be a substantial cost of production, and can have substantial environmental impact.

SUMMARY DISCLOSURE OF THE INVENTION

A hot-water immersion sanitizing system has a primary basin for receiving an unsanitary tool or machine component; a thermostatically-controlled valve with a first temperature setpoint, configured to conduct water from a hot water water source to the primary basin until a thermocouple senses a temperature within the primary basin has reached at least the first temperature setpoint, to interrupt flow to the primary basin upon the thermocouple sensing at least the first temperature setpoint; and an overflow drain to exhaust water while the thermostatically-controlled valve is open; thereby automatically maintaining temperature of water held in the primary basin for immersion sanitizing tools and parts at a water temperature of the first temperature setpoint or greater while automatically selectively interrupting flow of water from the water source under thermostatic control.

BRIEF DESCRIPTION OF THE DRAWINGS

The description set forth herein is illustrated by the several drawings, which are not necessarily drawn to mechanical scale.

DETAILED DESCRIPTION OF EMBODIMENT(S) OF THE INVENTION

The inventor of the present invention has recognized a problem in the art not previously recognized or addressed in the technology of tool and component sanitization for meat processing, handling, preparation and butchering, such as pork, seafood, poultry and beef plants. Handling and processing tools, such as knives and cutters, are typically sanitized after a tool or component has been exposed to an unsanitary portion of an item being processed, such as a bowel or lymph system. According to current facility design and practice, the knife, tool or component is temporarily immersed in hot water, such as water at 180° F., after which it is considered sanitary and ready to be used again in the processing.

The present inventor observed that this immersion sanitization typically involves an immersion vessel into which the tool, knife or part is immersed, and which is continuously fed with hot water from a processing plant's boiler system. This water is typically slightly hotter than the target temperature, such as 188° F., to allow for cooling while in the immersion vessel, while in the pipes. The water runs continuously, so that a portion of the water flows into a drain continuously, thereby refreshing the cooler water in the vessel with the hotter water from the supply source. The inventor, however, noted how wasteful this was, especially in the aggregate for an entire processing facility, of both water and energy to heat the water. Further, the present inventor's expertise led him to know that there is no government or standard that requires the sanitizing hot water to be free running or continuously flushing, only that it must be at a certain minimum temperature and that the tool are machine part must be immersed for a minimum period of time before being re-used.

Various embodiments of the present invention will enable adopters to retrofit existing processing facilities and to design new processing facilities to avoid wasteful free-running sanitizer stations, to realize more efficient usage of water and energy for heating the water. While the present embodiments disclosed in the following paragraphs will be made with reference to a sanitizing regimen of immersion into 180° F. water, it will be within the skill of those in the art to adjust this temperature for other embodiments, as well, without departing from the spirit and the scope of the present invention. The setpoint of 180° F. is appropriate for several types of meat processing including, for example, pork processing.

Figure 1:
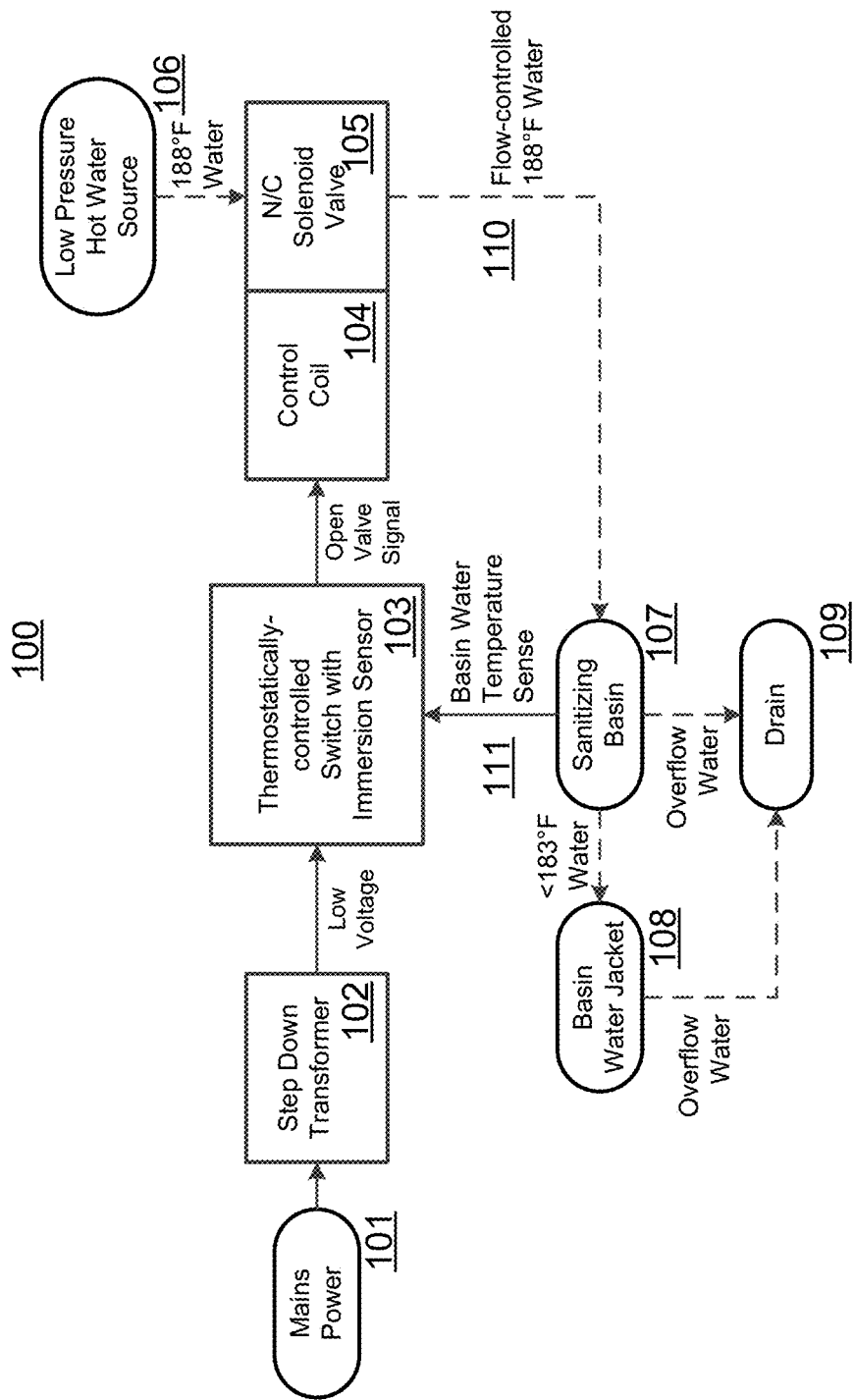
FIG. 1 provides a functional block diagram of at least one embodiment according to the present invention.

Referring now to FIG. 1, a functional arrangement 100 of components is shown according to at least one embodiment of the present invention. A thermostatically-controlled switch 103 sends a low-voltage control signal, such as 24 $V_{AC}$, to a control coil 104, to cause a normally-closed solenoid valve 105 to open, thereby allowing hot water to flow from a hot water source 106, such as a plant boiler system. This hot water is received into a sanitizing vessel 107, until the probe of the thermostatically-controlled switch 103 senses 111 the water in the basin 107 has reached a minimum target temperature. When the minimum target temperature of the water in the basin has been achieved as sensed 111 by the sensing element of the thermostatically-controlled switch 103, the thermostatically-controlled switch 103 removes the control signal from the control coil, thereby allowing the solenoid valve 105 to assume its normal closed position, and discontinuing the flow of the hot water from the hot water source 106 to the sanitizing basin 107. At this time, the sanitizing vessel 107 is full of water which meets or exceeds a minimum temperature for tool or part immersion for sanitizing.

During refilling (valve is open), excess water in the sanitizing basin 107 may overflow into a drain 109, thereby maintaining a water level within the sanitizing vessel set by the drain inlet in the vessel. In embodiments such as this, the water flow is thermostatically interrupted rather than flowing continuously as in the systems of the present technology, thereby meeting the hot water immersion sanitizing requirements which consuming less water and less energy to heat the water.

In at least one enhanced embodiment according to the present invention, the overflowing water from the immersion sanitizing vessel 107 is not directed immediately to a drain 109, but instead, is captured into and detained by a basin water jacket 108, wherein the warm water is held to provide a warm surrounding of a portion of the immersion sanitizing basin to further reduce heat loss from the sanitizing basin through one or more of the basin's bottom and/or sides. The level of the exhausted water in the water jacket 108 is determined by a drain inlet in the jacket itself. In such a jacketed solution, energy and water usage is further minimized, whereas the water in the sanitizing basin 107 will not cool off as fast as in the unjacketed embodiments, leading to longer periods of time of the solenoid valve 105 being closed, rather than open. This will further reduce water consumption as well as further reduce heating energy consumption.

In at least one embodiment fabricated and tested by the inventor for the purposes of water immersion at 180° F., the hot water source 106 for a typical processing plant was measured to be 188° F. in practice. The inventor employed a Honeywell™ L4006 Aquastat™ controller for the thermostatically-controlled switch 103, which closes a single-pole, single-throw (SPST) switch when its sensing element senses a setpoint adjusted to 183° F. This is 3° F. above the minimum target temperature of 180° F. to provide for proactively opening the solenoid valve, and to provide for some loss of heat during the filling process. The sensing element of the thermostatically-controlled switch 103 was immersed into the sanitizing basin in a manner suitable for sensing a typical temperature of the water throughout the sanitizing basin, but so as not to interfere with the immersion and removal of knives, tools, and machine parts. The inventor employed a Parker™ G23 24V general purpose solenoid coil as the control coil 104 to receive a control signal from the thermostatically-controlled switch 103, and the control coil 104 was mechanically and electrically coupled to a Parker™ GP400 general purpose solenoid valve as the normally-closed solenoid valve 105. A JARD™ 4031M 5:1 ($240V_{AC}$:$24V_{AC}$) 40VA control transformer was utilized as the step down transformer 102 to provide low-voltage from the mains power 101. Other configurations using alternative components are within the skill in the art to determine to realize alternative embodiments within the spirit and scope of the present invention.

Figure 2:
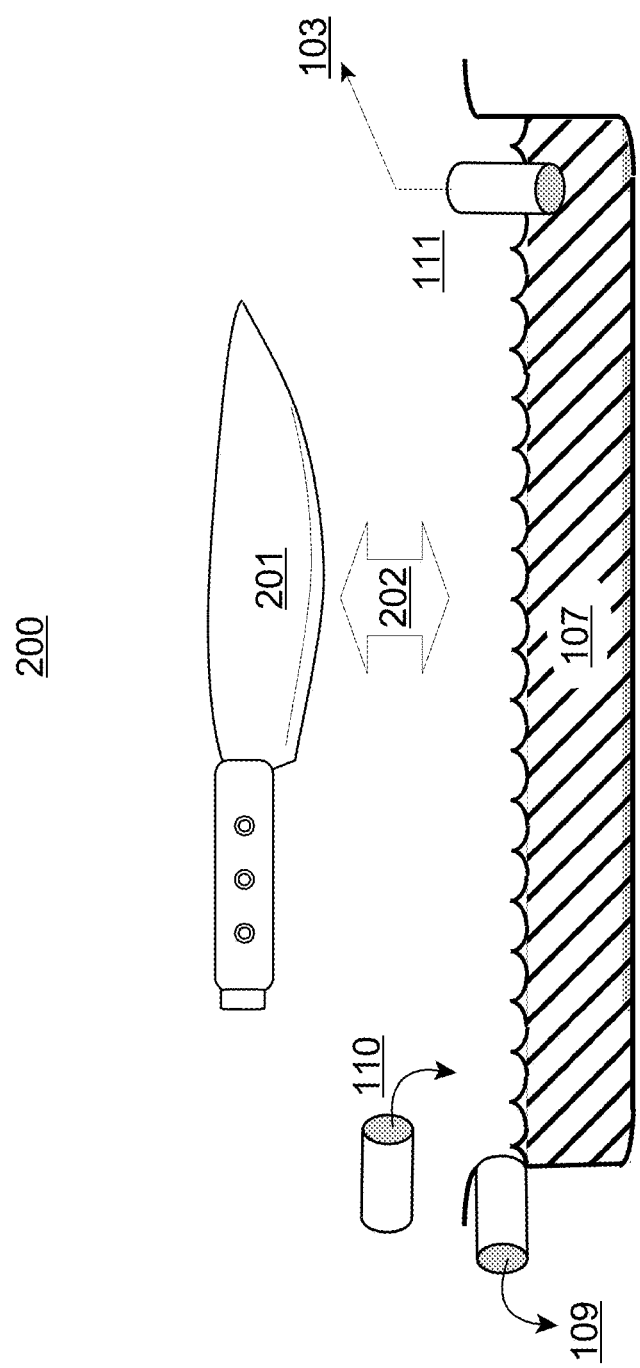
FIG. 2 illustrates an immersion vessel of at least one embodiment according to the present invention.

Referring now to FIG. 2, an exemplary configuration 200 as previously described is shown with a sanitizing vessel (basin) 107 receiving flow-controlled hot water 110 into the vessel 107 until it reaches a pre-determined depth, such as a mechanical level set by a drain 109. Other depth-control options are available, such as a float-switch wired into the configuration appropriately. A temperature sensor 111 is immersed into the sanitizing basin's water, to send the appropriate signal to the thermostatically-controlled switch 103. The tool or part, such as a knife 201, is sanitized by immersing 202 part or all of it into the water in the sanitizing basin 107, thereafter, removing it. The thermostatically-controlled switch 103 will sense 111 when the water in the basin 107 is cooling to the minimum setpoint, such as 183° F., at which time the flow-controlled hot water, such as 188° F. water, will begin to flow 110 into the basin 107, causing overflow into the drain 109, until the sensor 111 determines that the basin's water has reached an upper temperature limit. A thermostatically-controlled switch 103 such as a Honeywell Aquastat™ provides an upper temperature threshold, such as 188° F., until which it will keep its SPST switch closed. This is known as a "breaks on rise" feature—the switch closes upon sensing 183° F. and stays closed until sensing 188° F. This creates a hysteresis within the control method of the valve such that it does not toggle on and off (open and closed) rapidly as the water temperature bounces between 183° F. and 184° F. Using this hysteresis effect, the water flow is opened for a longer period of time to provide more water such that the basin's temperature is raised all the way up to the upper setpoint, such as 188° F., and then the valve is kept closed for a longer period of time while the water cools 6° F. to 183° F. This causes less wear on the valve itself, and creates fewer mechanical impulses into the plumbing system of the hot water source.

Figure 3:
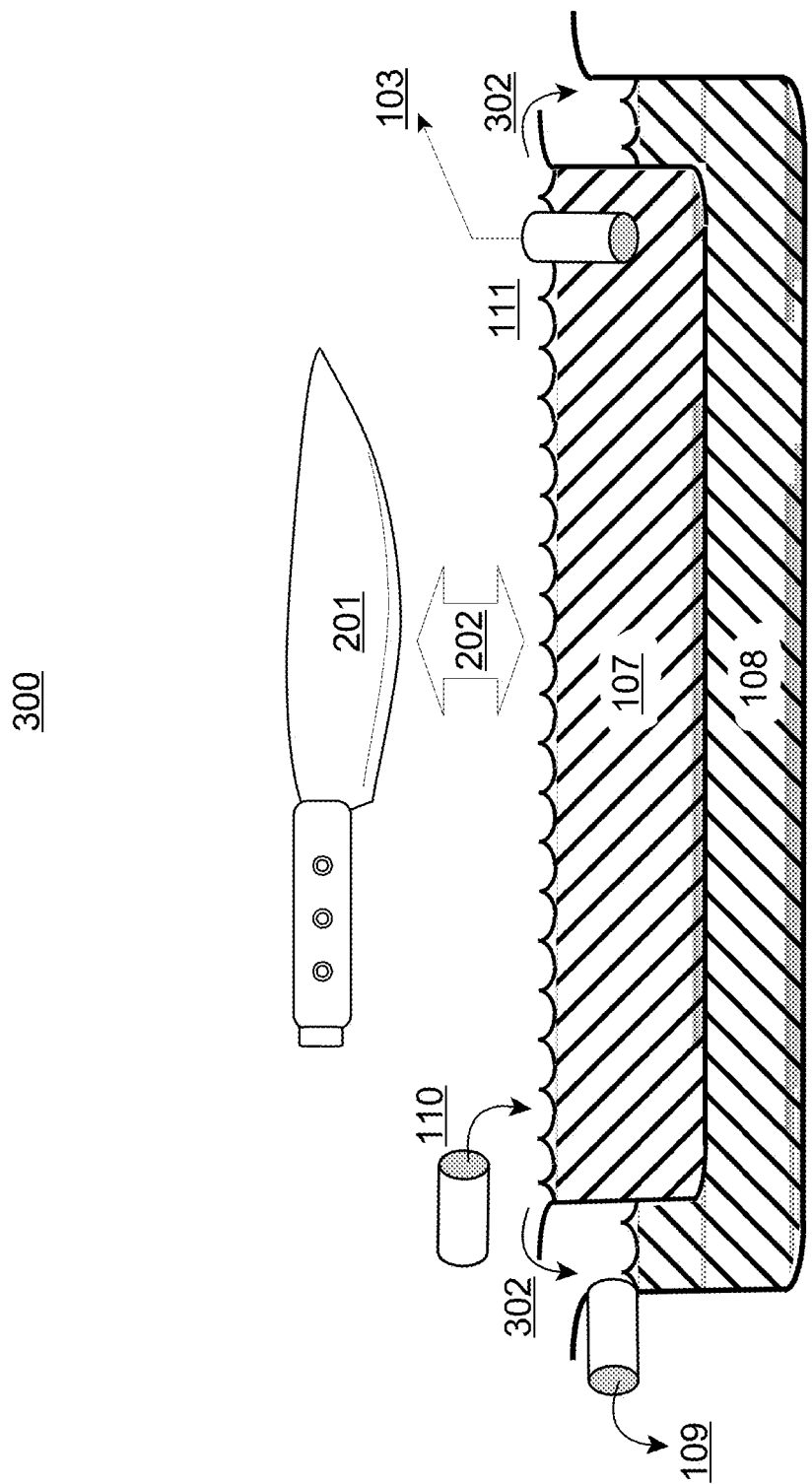
FIG. 3 illustrates an enhanced immersion vessel of at least one embodiment according to the present invention.

Turning now to FIG. 3, at least one enhanced embodiment according to the present invention is shown, in which the sanitizing basin 107 is at least partially surrounded, such as on the bottom and on one or more sides, by a secondary overflow basin 301 which forms a water jacket for the sanitizing basin 107. This water jacket is filled by the overflow 302 from the sanitizing basin 107 with the warm water which has reached the minimum temperature threshold, such as 183° F. This creates an enhanced thermal barrier for radiated heat from the bottom and/or side(s) of the primary sanitizing basin, even if the contents of the water jacket are below the target temperature of the sanitizing operation, it further slows the loss of heat, and thus, further reduces the usage of water and energy. This can be a significant improvement in performance in some embodiments, given that many configurations will use stamped stainless steel sheet metal for at least the primary (sanitizing) basin, and often also for the secondary (water jacket) basin. Such sheet metal is thermally conductive, not insulating, and therefore, sheds or loses heat from the water into the surrounding air quickly. The water jacketed embodiment of the present invention maintains the ability to clean (sterilize) stainless steel pans according to known methods, while improving the performance of the embodiment of the invention.

Conclusion. The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof, unless specifically stated otherwise.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

It will be readily recognized by those skilled in the art that the foregoing example embodiments do not define the extent or scope of the present invention, but instead are provided as illustrations of how to make and use at least one embodiment of the invention. The following claims define the extent and scope of at least one invention disclosed herein.

What is claimed is:

1. A sanitizing system for instantaneous hot water immersion of an unsanitary food preparation tool comprising:
   a primary open-top {i.e. unpressurized} basin having a bottom and one or more surrounding walls to form a vessel with a depth;
   a probe which determines a present temperature of first liquid contained in the primary basin;
   a switch configured to receive a signal from the probe, and to generate a valve-open signal when the present temperature falls to a first temperature value;
   a controllable valve receiving a second liquid at a predetermined food-grade instantaneous immersion sanitizing temperature, thereby allowing the second liquid to flow into the first liquid within the open-top primary basin responsive to receiving the valve-open signal, and interrupting the flowing responsive to not receiving the valve-open signal; and
   a first overflow drain to exhaust water from the primary basin responsive to overfilling during the open-valve flowing;
   thereby automatically maintaining the present temperature of the first liquid held in the primary basin at a temperature for food-grade instantaneous immersion sanitization of food preparation tools and machine parts;
   wherein the first liquid and the second liquid consist essentially of water.

2. The sanitizing system as set forth in claim 1 wherein the switch is further configured to discontinue the generating of the valve-open signal responsive to the present temperature rising to a second temperature value, wherein the second temperature value is greater than the first temperature value, thereby providing a positive basin water temperature differential between valve opening and closing thresholds of the thermostatically-controlled valve.

3. The sanitizing system as set forth in claim 2 in which the second temperature value comprises 188° F.

4. The sanitizing system as set forth in claim 1 in which the first temperature value comprises 183° F.

5. The sanitizing system as set forth in claim 1 further comprising a secondary vessel configured to receive exhaust water from the first overflow drain, and to detain the received exhausted water adjacent to at least a bottom of the primary basin, thereby allowing heat from the detained water to rise from the secondary vessel to the primary basin.

6. The sanitizing system as set forth in claim 5 wherein the first overflow drain comprises a lip or rim of the primary basin.

7. The sanitizing system as set forth in claim 6 further comprising a second overflow drain configured to maintain a water level in the secondary vessel.

\* \* \* \* \*